United States Patent
Bergey et al.

(10) Patent No.: US 8,035,016 B2
(45) Date of Patent: Oct. 11, 2011

(54) METHOD OF USING GOLD NANORODS-SIRNA COMPLEXES

(75) Inventors: Earl J. Bergey, South Dayton, NY (US); Adela Bonoiu, N. Tonawanda, NY (US); Supriya Mahajan, Amherst, NY (US); Paras N. Prasad, Williamsville, NY (US); Indrajit Roy, Amherst, NY (US); Stanley A. Schwartz, East Amherst, NY (US); Ken-Tye Yong, Tonawanda, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 12/555,609

(22) Filed: Sep. 8, 2009

(65) Prior Publication Data

US 2010/0125100 A1 May 20, 2010

Related U.S. Application Data

(60) Provisional application No. 61/094,532, filed on Sep. 5, 2008.

(51) Int. Cl.
*A61P 43/00* (2006.01)
*C12N 15/113* (2010.01)

(52) U.S. Cl. .................... 977/773; 514/44 A

(58) Field of Classification Search ............ 514/44 A; 977/773

See application file for complete search history.

(56) References Cited

U.S. PATENT DOCUMENTS

2006/0058255 A1 3/2006 Chen et al.
2008/0199531 A1 8/2008 Salem et al.

OTHER PUBLICATIONS

Roy et al.; Non-viral gene transfection nanoparticles: Function and applications in brain; Nanomedicine, Jun. 2008, vol. 4, No. 2; pp. 89-97.
Niidome et al.; Preparation of primary amine-modified gold nanoparticles and their transfection ability into cultivated cells; Chem. Commun., Sep. 7, 2004, vol. 17; pp. 1978-1979.
Ding et al.; Gold Nanorods Coated with Multilayer Polyelectrolyte as Contrast Agents for Multimodal Imaging; J. Phys. Chem., 2007, vol. 111, No. 34; pp. 12552-12557.

*Primary Examiner* — J. E. Angell
(74) *Attorney, Agent, or Firm* — Hodgson Russ LLP

(57) ABSTRACT

Provided are methods and compositions for inhibiting expression of one or more target genes. The compositions contain RNA polynucleotides that can inhibit expression of a target gene via RNA interference (RNAi) electrostatically complexed with surface functionalized gold nanorods (GNRs). The RNA polynucleotides are not covalently bound to the surface functionalized GNRs. The method involves inhibiting expression of a target gene in an individual. The method is performed by administering to the individual an effective amount of a composition containing surface functionalized GNRs electrostatically complexed with RNA polynucleotides, such as siRNA, that can inhibit expression of the target gene via RNAi. The siRNA is not covalently bound to the surface functionalized GNRs.

7 Claims, 11 Drawing Sheets

SEQUENCE LISTING

```
<160> NUMBER OF SEQ ID NOS: 2

<210> SEQ ID NO 1
<211> LENGTH: 25
<212> TYPE: RNA
<213> ORGANISM: human

<400> SEQUENCE: 1
acacaccacc uucgcugaaa gcugu                                           25

<210> SEQ ID NO 2
<211> LENGTH: 25
<212> TYPE: RNA
<213> ORGANISM: human

<400> SEQUENCE: 2
acagcuuuca gcgaaggugg ugugu                                           25
```

METHOD OF USING GOLD NANORODS-SIRNA COMPLEXES

This application claims priority to U.S. application No. 61/094,532, filed Sep. 5, 2008, the disclosure of which is incorporated herein by reference.

This invention was supported by grant numbers RO1 CA129111, CA 099326 and R21 CA121848 from the National Institutes of Health. The U.S. government may have certain rights in the invention.

FIELD OF THE INVENTION

The invention relates generally to inhibiting expression of genes, and more specifically to inhibiting gene expression using compositions comprising gold nanorods electrostatically complexed to siRNAs.

BACKGROUND OF THE INVENTION

Nanotechnology is having an increasing impact in the healthcare industry, offering unprecedented capability of not only carrying multiple diagnostic/therapeutic payloads in the same composition, but also facilitating the targeted delivery into specific sites and across complex biological barriers.

RNA interference (RNAi) mediated silencing or down-regulation of mRNA is an established technique for inhibiting gene expression. However, a major hurdle limiting the use of the gene silencing technology is the lack of methods to safely and efficiently deliver siRNA molecules to target cells/tissues. In free form, siRNA molecules have a very short half life in physiological conditions, owing to their vulnerability for degradation by endogeneous nucleases. In addition, their permeability across cellular membranes is extremely limited. Furthermore, free siRNA is completely inaccessible to the brain, which is a major target organ for the delivery of various siRNA-based therapeutics. The brain is secluded from the systemic circulation owing to the presence of the blood brain barrier (BBB), which excludes the brain specific delivery of 100% of large-molecule neurotherapeutics and more than 98% of all small-molecule drugs (Pardridge W M (2007). Advanced Drug Delivery Reviews 59(2-3):141-152). Therefore, there is a need ongoing need for improved compositions and methods for siRNA delivery, which will not only protect the siRNA from physiological degradation, but also help them permeate across biological barriers such as cellular membranes and the BBB.

SUMMARY OF THE INVENTION

The invention provides methods and compositions for inhibiting expression of one or more target genes. The compositions comprise RNA polynucleotides that can inhibit expression of a target gene via RNA interference (RNAi) electrostatically complexed with surface functionalized gold nanorods (GNRs). The RNA polynucleotides are not covalently bound to the surface functionalized GNRs.

The method comprises inhibiting expression of a target gene in an individual. The method is performed by administering to the individual an effective amount of a composition comprising surface functionalized GNRs electrostatically complexed with RNA polynucleotides, such as siRNA, that can inhibit expression of the target gene via RNAi. The siRNA is not covalently bound to the surface functionalized GNRs.

The gold nanorods have a length of from 10 to 100 nm, inclusive, and including all integers there between. The GNRs have a diameter of from 5 to 45 nm inclusive, and including all integers there between. The GNRs can be pure gold, or may be from 90% to 99%, inclusive, including all integers there between, pure gold.

The GNRs can be made by any suitable method. In one embodiment, seed mediated growth using cetyltrimethylammonium bromide (CTAB) is used. Alternatively, GNRs that can be surface functionalized for the invention are available from NANOPARTZ (Salt Lake City Utah) or NANORODS, LLC (Maryland).

The surfaces of the gold nanorods are functionalized so as to have a positive zeta potential suitable for electrostatically complexing the GNRs with RNA polynucleotides, such siRNA. The surfaces of the gold nanorods can be functionalized with bifunctional molecules, such as thiolated-PEG-NH2 or thiolated-PEG-COOH, or they may be coated with first with an anionic polyelectrolyte, such as poly(3,4-ethylenedioxythiophene)/poly(styrenesulfate) (PEDT/PSS), and then with the cationic polyelectrolyte poly(diallyldimethyl ammonium chloride) (PDDAC). This results in gold nanorods with positive zeta potential and also masks the CTAB layer. The surface functionalization results in the formation of multilayered gold nanorods which can have a positive zeta potential of from +29.9 mV to +21.3 mV, inclusive, and including all integers there between, and all numbers between consecutive integers to the tenth decimal point, at the physiological pH (pH 7.0). When electrostatically complexed to RNA polynucleotides, the complexes have a lower positive zeta potential. For example, at a pH of 7.0, the zeta potential of the surface functionalized gold nanorods electrostatically complexed to RNA polynucleotides is 3.9 to 0.7 mV, inclusive, and including all integers there between, and all numbers between consecutive integers to the tenth decimal point.

The positively charged gold nanorods are electrostatically complexed to the RNA polynucleotides using electrostatic interactions. In various embodiments, between 10%-100%, inclusive, and including all integers there between, of the surface functionalized GNRs are electrostatically complexed, but not covalently bound, to RNA polynucleotides.

The RNA polynucleotides that are electrostatically complexed to the gold nanorods to form nanoplexes can be any RNA polynucleotides. It is preferable to use siRNA. In one embodiment, a composition of the invention comprises as a ratio, for every 50 pmols of siRNA, 0.3-0.5 pmols, inclusive, including all integers there between, and all numbers between consecutive integers to the tenth decimal point, of gold nanorods. A wide variety of siRNAs are commercially available, and it is expected that the invention can be used with any siRNA to inhibit expression of any target gene in an individual, including without limitation any gene expressed in any tissue type of the individual. For example, the target gene could be a gene involved in any disease, such as cancer, autoimmune, neuromuscular, neuromotor, psychiatric, psychological, neurological, behavioral or other cognitive disorders. In one embodiment, genes involved in the dopaminergic signaling pathway can be target genes for therapy of substance addiction.

Using the compositions and methods of the invention, we demonstrate that GNRs electrostatically complexed with, but not covalently bound to, siRNA molecules can be used to inhibit expression of target genes in vitro and in vivo. For example, we show inhibition of the DARPP-32 gene in dopaminergic neuronal (DAN) cells in vitro using nanoplexes comprising siRNA targeting the DARP-32 gene. We demonstrate that this inhibition is greater than that obtained using commercially available siRNA delivery reagent (siPORT), and that the inhibition of expression of the DARP-32 target gene also inhibits expression of downstream genes in the dopaminergic signalling pathway. We also demonstrate >70% inhibition of a model target gene glyceraldehyde 3-phosphate dehydrogenase (GAPDH) in vivo in rat brain using compositions and methods of the invention.

DETAILED DESCRIPTION OF THE INVENTION

Figure 1:
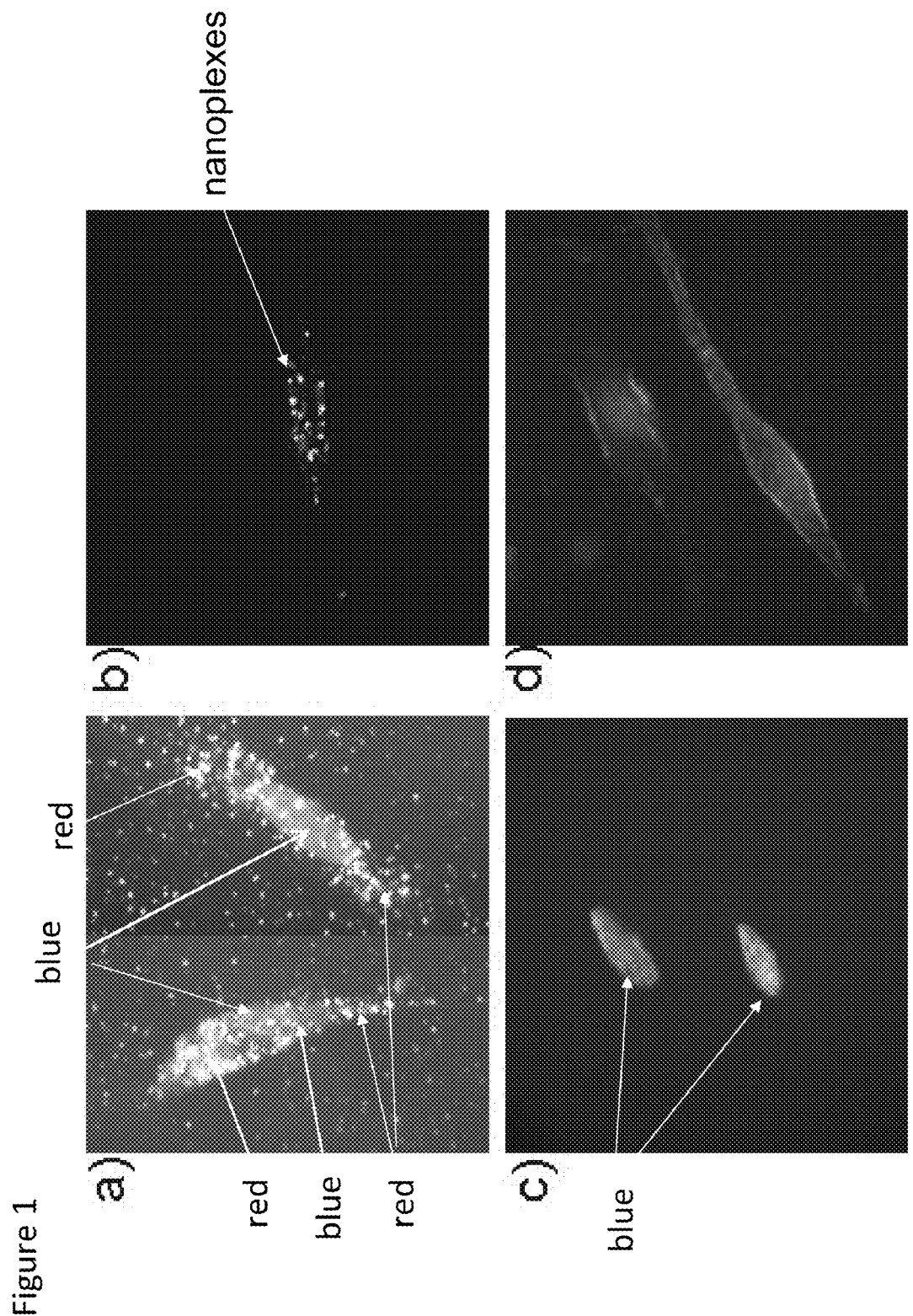
FIG. 1 presents imaging analysis of functionalized GNR-siRNA nanoplex uptake in DAN cells. Dark field images with hoechst nuclear staining (a and c), and confocal images (b and d) of DAN cells, following treatment with fluorescently labeled siRNA (siRNA$^F$), either in free form (c and d), or complexed with GNRs (a and b). The dark field images of GNRs corresponding to the longitudinal surface plasmonic enhancement in the red region can be clearly distinguished from the background (a). Confocal images show robust uptake of the siRNA$^F$ complexed with GNRs (b), as opposed to free siRNA$^F$ (c).

The present invention provides methods and compositions for inhibiting expression of one or more target genes. The compositions comprise surface functionalized gold nanorods (GNRs) electrostatically complexed with RNA polynucleotides that can inhibit expression of a target gene via RNA interference (RNAi). The RNA polynucleotides are not covalently bound to the gold nanorods.

The method comprises inhibiting expression of a target gene in an individual by administering to the individual an effective amount of a composition comprising surface functionalized GNRs electrostatically complexed with, but not covalently bound to, RNA polynucleotides that can inhibit expression of the target gene via RNAi. In another embodiment, a method of the invention comprises inhibiting expression of a target gene by contacting a cell with an effective amount of a composition comprising surface functionalized GNRs electrostatically complexed with, but not covalently bound to, RNA polynucleotides that can inhibit expression of the target gene via RNAi.

The gold nanorods for use in the compositions and methods of the invention have a length of from 10 to 100 nm, inclusive, and including all integers there between. In one embodiment, the GNRs have an average length of from 70-75 nm. The GNRs have a diameter of from 5 to 45 nm inclusive, and including all integers there between. In one embodiment, the GNRs have an average diameter of 25-30 nm.

The GNRs can be pure gold, or may be from 90% to 99%, inclusive, including all integers there between, pure gold. In various embodiments, the GNRs may contain up to 1% silver on their surfaces, and may contain in cetyltrimethylammonium bromide (CTAB). In this regard, GNRs can be made by any suitable method. For example, electrochemical synthesis in solution, membrane templating, photochemical synthesis, microwave synthesis, and seed mediated growth are all suitable and non-limiting examples of methods of making the GNRs. In one embodiment, the gold nanorods are made using the seed-mediated growth method in cetyltrimethylammonium bromide (CTAB). Alternatively, GNRs for use in the invention can be obtained from NANOPARTZ (Salt Lake City Utah) or NANORODS, LLC (Maryland).

In order to form complexes of the gold nanorods and the RNA polynucleotides, the surfaces of the gold nanorods are functionalized so as impart a positive zeta potential suitable for electrostatically complexing the GNRs with RNA polynucleotides, such siRNA. Any suitable method of creating a positive zeta potential on the gold nanorods may be used. For example, the surfaces of the gold nanorods can be functionalized with bifunctional molecules, such as thiolated-PEG-NH2 or thiolated-PEG-COOH. In one embodiment, the surface functionalization is achieved by coating the CTAB-coated gold nanorods first with the anionic polyelectrolyte poly(3,4-ethylenedioxythiophene)/poly(styrenesulfate) (PEDT/PSS), then with the cationic polyelectrolyte poly(diallyldimethyl ammonium chloride) (PDDAC). This results in gold nanorods with a cationic surface charge (positive zeta potential), and also masks the CTAB layer, which is believed to be toxic and therefore not useful for delivering the RNA polynucleotides without the surface functionalization as disclosed herein. The surface functionalization results in the formation of multilayered gold nanorods, which, in one embodiment, have a positive zeta potential of from +29.9 mV to +21.3 mV, inclusive, and including all integers there between, and all numbers between consecutive integers to the tenth decimal point, at the physiological pH (pH 7.0). However, when electrostatically complexed to RNA polynucleotides according to the invention, the complexes have a lower positive zeta potential. In particular, in one embodiment, at a pH of 7.0, the zeta potential of the gold nanorods electrostatically complexed to RNA polynucleotides is 3.9 to 0.7 mV, inclusive, and including all integers there between, and all numbers between consecutive integers to the tenth decimal point. This residual positive charge is believed to be required in order to achieve efficient cellular entry of the resulting siRNA/GNR nanoplexes, which, in the absence of a suitable biorecognition molecule, often proceeds via electrostatic interaction involving the anionic cellular membrane and sparsely positive nanoparticle/nanoplex. One of the major problems associated with nanoparticles/nanoplexes injected systemically in the body, particularly when they have a large cationic charge on their surface, is their capture by the reticuloendothelial system (RES) of the body, leading to their reduced bioavailability and accumulation in non-target organs such as liver and spleen. Since the nanoplexes described here have a residual, but not large positive charge, they well suited to evade RES capture. (Davis SS (1997) Trends Biotechnol 15(6):217-224).

In one embodiment, to obtain gold nanorods having a positive zeta potential, gold nanorods can be subjected to sequential coating with two successive layers of polyelectrolytes, the first layer having a negative charge, and the second having a positive charge. For example, gold nanorods can be subjected to sequential coating using negatively charged Poly(3,4-ethylenedioxythiophene)/poly(styrenesulfate) (PEDT/PSS) and positively charged poly(diallyldimethyl ammonium chloride) (PDDAC) according to known methods (see, for example, Ding et al. (2007) J. Phys. Chem. C 34(111):12552-12557}.

The positively charged gold nanorods are electrostatically complexed to the RNA polynucleotides using electrostatic interactions. By gel electrophoresis and Zeta-potential analysis, we have standardized our procedure where 100% of the surface functionalized gold nanorods can be complexed with siRNA. However, we can also tune the conditions to achieve 10-100% complexation. Thus, in various embodiments of the invention, between 10%-100%, inclusive, and including all integers there between, of the surface functionalized GNRs are electrostatically complexed, but not covalently bound, to RNA polynucleotides, such as siRNA. Thus, 20%, 30%, 40%, 50%, 60%, 70%, 80%, 90%, 95%, or more, and up to 100%, of the surface functionalized GNRs in a composition of the invention can be electrostatically complexed with siRNA.

We confirmed formation of nanoplexes from an observed red-shift in localized longitudinal plasmon resonance peak of the gold nanorods, as well as from restricted electrophoretic mobility of the nanoplexes using gel electrophoresis. The uptake of the nanoplexes into the DAN cells in vitro was demonstrated using plasmonic enhanced dark field imaging of the gold nanorods, as well as confocal microscopy and fluorimetric analysis of cell lysates. We also demonstrate that the nanoplexes have higher transmigration efficiency across an in-vitro blood brain barrier (BBB) model over that of free siRNA, without compromising the functional integrity of the barrier. Moreover, we demonstrate inhibition of a model target gene (GAPDH) in vivo in rat hippocampus using compositions and methods of the invention. Specifically, we achieved >70% suppression of GAPDH gene expression in the CA1 region and in the combined CA3/dentate gyms regions of the hippocampus at 4 days post-injection of nanoplexes comprising GNRs electrostatically complexed with siRNA targeting GAPDH, and this level of suppression was maintained for at least 11 days post-injection of the nanoplexes.

In the present invention, we demonstrate that GNRs electrostatically complexed with, but not covalently bound to, siRNA molecules (also referred to herein as "nanoplexes") can be used to inhibit expression of target genes in vitro and in vivo. In particular, we demonstrate inhibition of the DARPP-32 gene in dopaminergic neuronal (DAN) cells in vitro using nanoplexes comprising siRNA targeting the DARP-32 gene. The efficiency of inhibition of DARPP-32, as well as other key downstream effector molecules of the dopaminergic signalling pathway, such as ERK and protein phosphatase-1, using the DARPP-32 siRNA complexed with the GNRs, is shown to be greater than that obtained using commercially available siRNA delivery reagent (siPORT) delivering the DARPP-32 siRNA under the same conditions.

As used herein, "target gene" means any gene for which an inhibition of expression is desired. "Inhibition of expression" and "inhibiting expression" and "inhibits expression" and "inhibited expression" of a target gene each refers to decreasing the amount of mRNA encoded by a target gene. In this regard, since the invention takes advantage of RNAi, it is considered to function by facilitating RNAi-mediated degradation of mRNA expressed from a target gene. RNAi-mediated degradation of mRNA results in a decrease in the amount of the mRNA and the protein encoded by the target gene.

A decrease in mRNA and/or protein encoded by a target gene achieved by practicing the method of the invention can be a partial or a complete decrease. For example, practicing the method of the invention can result in a decrease of from 50% to 100%, inclusive, and including all integers there between, of target gene encoded mRNA and/or target gene encoded protein, relative to the amount of the target gene encoded mRNA and/or protein prior to or in the absence of performing the method of the invention. In particular embodiments, inhibiting the expression of the target gene comprises reducing an amount of mRNA encoded by the target gene in a plurality of cells in the individual by at least 60%, or at least 70%, or at least 80%, or at least 90%, or at least 100%, relative to the amount of mRNA encoded by the target gene in the plurality of cells prior to the administering the composition to the individual.

Inhibiting expression of a target gene effected by performing the method of the invention can be detected by measuring a decrease in the amount of target gene encoded mRNA and/or target gene encoded protein present in the individual, such as in a particular tissue or fluid in the individual, or in a biological sample obtained from an individual. The biological sample could be any biological material in which the target gene is expressed.

If desired, in order to measure inhibition of expression of a target gene, the amount of target gene encoded mRNA and/or protein in a particular tissue or fluid in the individual or in a biological sample taken from an individual to whom a composition of the invention is administered can be compared to a control. Non-limiting examples of suitable controls include target gene encoded mRNA and/or protein present in the tissue or fluid in the individual or in a biological sample obtained from the individual before performing the method of the invention. Alternatively, the control could be target gene encoded mRNA and/or protein in, or a biological sample obtained from, another individual to whom a composition of the invention is not administered and who is matched for age, sex, disease, tissue type, and/or other characteristics that will be recognized by those skilled in the art. The control could also be a standardized amount of mRNA or protein produced by the target gene.

The RNA polynucleotides that are electrostatically complexed to the gold nanorods to form nanoplexes can be any RNA polynucleotides, including siRNA or shRNA. It is preferable to use siRNA. As is known in the art, siRNA comprises a duplex region containing a sense strand annealed to an antisense strand in an anti-parallel configuration. The sense strand and antisense strands are fully complementary to each other over the duplex region, but for an overhang at the end of each strand that may be present. The overhang is generally a two nucleotide overhang, but can be up to six nucleotides in length. Thus, the sense and antisense strands are distinct RNA polynucleotides. Each of the polynucleotides can consist of between 21-30 nucleotides, inclusive, and including all integers between 21 and 30. Accordingly, a composition of the invention suitable for use in the invention comprises surface functionalized gold nanorods electrostatically complexed to siRNAs. There is no need to covalently bind the surface functionalized GNRs to RNA. Accordingly, no additional steps are carried out to covalently bind the GNRs to siRNA, and thus a composition of the invention can comprise, consist essentially of, or consist of, siRNA electrostatically complexed to, but not covalently bound to gold nanorods.

In one embodiment, gold nanorods are electrostatically complexed to siRNA, wherein the siRNA consists of a duplex region and either no overhangs, or at least one overhang, wherein the overhang comprises six or fewer nucleotides, and wherein the duplex region consists of a sense region and an antisense region, wherein the sense region and the antisense region together form the duplex region, and the duplex region is 19-30 base pairs in length. The sense region contains an RNA sequence that is identical to the sequence of the mRNA encoded by the target gene.

In one embodiment, a composition of the invention comprises, as a ratio, for every 50 pmols of siRNA, 0.3-0.5 pmols, inclusive, including all integers there between, and all numbers between consecutive integers to the tenth decimal point, of gold nanorods.

As an alternative to siRNA, a single RNA polynucleotide in the form of an shRNA can also be electrostatically complexed to the gold nanorods. As is known in the art, shRNAs adopt a typical secondary structure that contains a duplex region, and a short loop sequence between joining the duplex region. shRNA, when delivered to the cytoplasm, is processed by dicer into siRNAs. The siRNAs are then recognized by RNA-induced silencing complex (RISC), and once incorporated into RISC, the siRNAs facilitate cleavage and degradation of target mRNA.

As will be recognized by those skilled in the art, a wide variety of siRNAs and shRNAs targeted to the majority of human, rat, and mouse genes are commercially available. For example, SANTA CRUZ BIOTECHNOLOGY offers siRNAs targeted to 23,775 human genes, which is believed to represent 100% of all putative protein-encoding human genes; AMBION also offers pre-designed siRNAs directed to essentially all human, mouse, and rat genes; SIGMA offers a lentivirus-based shRNA library containing over 150,000 pre-cloned shRNA vectors targeting more than 15,000 human and 15,000 mouse genes. It is expected the present invention will function with any of these commercially available reagents. Further, any shRNA sequence can be used as the basis for designing an siRNA sequence according to routine techniques.

RNA polynucleotides that can be used for the compositions and methods of the invention can be made using any acceptable technique, including conventional and commercially available chemical synthesis techniques. The polynucleotides can also be expressed from expression vectors, and isolated and purified as necessary. Further, various types of polynucleotide modifications are contemplated so as to improve the capability of the polynucleotides to resist endonuclease degradation and/or improve cleavage of their target gene mRNAs. For example, in addition to RNA, the polynucleotides can comprise RNA:DNA hybrids. Other modifications that can be comprised by the polynucleotides include but are not limited to modified ribonucleotides or modified deoxyribonucleotides. Such modifications can include without limitation substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In addition to phosphodiester linkages, the nucleotides can be connected by a synthetic linkage, i.e., inter-nucleoside linkages other than phosphodiester linkages, provided the appropriate zeta potential of the gold nanorod/RNA polynucleotide complexes is maintained, as discussed further below.

The invention is expected to be effective for inhibiting the expression of any target gene expressed in an individual, including without limitation any gene expressed in any tissue type of the individual. In non-limiting illustrative embodiments, the target gene could be a gene involved in any disease, such as cancer, including but not limited to cancers of the brain, breast, prostate, kidney, lung, skin, colon, pancreas, thyroid, mouth, esophagus, bone, blood, lymph, or any other tissue or cell type. The target gene could also be involved in autoimmune, neuromuscular, neuromotor, psychiatric, psychological, neurological, behavioral or other cognitive disorders. For example, genes involved in the dopaminergic signaling pathway can be target genes for therapy of substance addiction. One example of such a gene is DARPP-32 (GenBank Accession No. AF464196; Jul. 23, 2002 entry). One example of a suitable siRNA for inhibiting expression of DARPP-32 according to the invention comprises as the sequence of the sense strand: ACA CAC CAC CUU CGC UGA AAG CUG U (SEQ ID NO:1) and as the sequence of the antisense strand: ACA GCU UUC AGC GAA GGU GGU GUG U (SEQ ID NO:2). Thus, in one embodiment, the invention comprises a composition comprising, consisting essentially of, or consisting of, surface functionalized gold nanorods electrostatically complexed with siRNAs having a sense strand that comprises or consists of SEQ ID NO:1 annealed to an antisense strand that comprises or consists of SEQ ID NO:2. An siRNA that consists of SEQ ID NO:1 annealed to SEQ ID NO:2 is referred to herein as GNR-siRNA$^D$ The siRNAs are not covalently bound to the GNRs. In another embodiment, the method of the invention comprises inhibition of DARPP-32 expression in an individual by administering to the individual an effective amount of a composition as described above such that expression of DARPP-32 is inhibited in the individual.

The invention also encompasses compositions comprising gold nanorods, each of which is electrostatically complexed to a plurality of first siRNAs capable of inhibiting a first target gene, and a second plurality of siRNAs capable of inhibiting a second target gene. Such a composition can be obtained by combining surface functionalized GNRs with a mixture of the first and second siRNAs according to methods described herein. Alternatively, the composition may comprise a first plurality of gold nanorods electrostatically complexed to siRNAs capable of inhibiting a first target gene, and a second plurality of gold nanorods electrostatically complexed to siRNAs capable of inhibiting a second target gene. The first and second target genes may be related or unrelated in function. The invention further encompasses inhibition of expression of more than two target genes.

The individual to which the composition of the invention is administered is a mammal. In one embodiment, the mammal is a human.

If desired, compositions comprising the nanoplexes may be prepared by mixing with any suitable pharmaceutically acceptable carriers, excipients and/or stabilizers. Some examples of compositions suitable for mixing with nanoplexes can be found in: *Remington: The Science and Practice of Pharmacy* (2005) 21st Edition, Philadelphia, Pa. Lippincott Williams & Wilkins.

It is expected that the compositions of the invention can be administered to an individual using any available method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. In one embodiment, a composition of the invention can be injected directly into a tissue that comprises a target gene, the inhibition of expression of which is desirable.

Administration of the compositions can be performed in conjunction with conventional therapies that are intended to treat a disease or disorder associated with the target gene. Thus, in various embodiments, the individual can be an individual that is in need of treatment for any disease or disorder, including but not limited to any of the diseases and disorders described herein.

The composition could be administered prior to, concurrently, or subsequent to conventional therapies for the diseases or disorder associated with expression of the target gene. For example, in the case of substance addiction, a composition of the invention could be administered in conjunction with any conventional therapeutic agent intended to provide therapy for the substance addiction, such as methadone administration to individuals addicted to opiates. Alternatively, if the target gene is involved in cancer, a composition of the invention could be administered in conjunction with anti-cancer therapies, including but not limited to chemotherapies, surgical interventions, and radiation therapy.

It will be recognized by those of skill in the art that the form and character of the particular dosing regime employed in the method of the invention will be dictated by the route of administration and other well-known variables, the sex and size of the individual, and the type and stage of the particular disease or disorder being treated. Based on such criteria, one skilled in the art can determine an amount of a composition described herein that will be effective to inhibit expression of the target gene.

Without intending to be bound by any particular theory, it is considered that subsequent to administration to an individual, the composition comprising the gold nanorods electrostatically complexed to the RNA polynucleotides is taken up by cells in the individual via the endocytic pathway. As is known to those skilled in the art, the endocytic pathway of mammalian cells involves distinct membrane compartments that internalize molecules from the plasma membrane. The main components of endocytic pathway can be characterized as the early endosomes, the later endosomes, and the lysosomes. The pH varies in each of these compartments, with the early endosomes mildly acidic, while the later endosomes generally have an internal pH of approximately 5.5 to 6.0. Later endosomes are believed to facilitate delivery of material to lysosomes, which have a pH of approximately 4.8, but can be lower, such as 4.0. Thus, it is considered that the siRNA dissociates from the surface functionalized gold nanorods in an intracellular aqueous medium in a cell of the individual, wherein the aqueous medium has a pH of from 4.0 to 6.0, including the integer there between, and all numbers between 4.0 to 6.0 to the tenth decimal point. Thus, it is also considered that the drop in pH in the endosomal and/or lysosomal compartments relative to the pH of the extracellular milieu facilitates access of the dissociated siRNAs to the cytoplasm, wherein they can participate in RNAi-mediated degradation of mRNA expressed from a target gene. It will therefore be recognized by those skilled in the art that this feature of the invention would be precluded by techniques where the RNA polynucleotides capable of inhibiting expression of a target gene are covalently bound to gold nanorods.

The following Examples are intended to illustrate but not limit the invention.

Example 1

This Example provides a description of the materials and methods used to obtain the data presented in the Examples 2-7.

Sequence of siRNA: The siRNA sequences for DARPP-32 (GenBank Accession No. AF464196; Jul. 23, 2002 entry, incorporated herein by reference) are: Sense-ACA CAC CAC CUU CGC UGA AAG CUG U (SEQ ID NO:1) Antisense-ACA GCU UUC AGC GAA GGU GGU GUG U (SEQ ID NO:2). The appropriate scrambled control siRNA sequences are, Sense-ACA CCC AUC CUC GGU AAG ACA CUG U (SEQ ID NO:3) and Antisense-ACA GUG UCU UAC CGA GGA UGG GUG U (SEQ ID NO:4).

Synthesis of the GNRs and GNR-siRNA nanoplexes: Cetyltrimethylammonium bromide (CTAB), hydrogen tetrachloroaurate(III) trihydrate (HAuCl4*3H2O), silver nitrate (AgNO3), L-ascorbic acid, glutaraldehyde (50% aqueous solution), and sodium borohydride were purchased from ALDRICH. All chemicals were used as received. HPLC-grade water was used in all the experiments. Stock solutions of sodium borohydride and L-ascorbic acid were freshly prepared for each new set of experiments. Poly(3,4-ethylenedioxythiophene)/poly(styrenesulfate) (PEDT/PSS) and poly (diallyldimethyl ammonium chloride) (PDDAC) were obtained from POLYSCIENCES. The GNRs were prepared by the seed-mediated growth method in CTAB solution, followed by their sequential coating with two successive layers of polyelectrolytes, (a) the negatively charged PEDT/PSS, and (b) the positively charged PDDAC, according to a known technique (Ding H et al. (2007) J. Phys. Chem. C 34(111): 12552-12557). The cationic GNR were then electrostatically attached to siRNA in OptiMEM media (INVITROGEN CORPORATION, Carlsbad, Calif.), resulting in the formation of the nanoplexes.

Characterization of GNRs and GNR-siRNA nanoplexes using Transmission Electron Microscopy (TEM) and UV-Visible absorbance and photoluminescence (PL) spectroscopy: TEM images were obtained using JEOL model JEM-100CX microscope, operating with acceleration voltage 80 kV. The specimens were prepared by drop-coating the sample dispersion onto a holey carbon-coated 200 mesh copper grid, which was placed on filter paper to absorb excess solvent.

The absorption spectra were collected using a Shimadzu model 3101PC UV-vis-NIR scanning spectrophotometer over the range from 300 to 800 nm. The samples were measured against water as reference. The PL spectra were collected using a Spectrofluorometer (Fluorolog®-3, Horiba Jobin Yvon).

Agarose Gel Electrophoresis: Nanoplexes of GNR with either siRNA$^D$ or siRNA$^F$, as well as equivalent amounts of free siRNA, were added in individual wells (100 pmols of siRNA per well) in 1.5 agarose gel casted in Tris acetate-EDTA (TAE) buffer. The gel was run for one hour at 100 volts, stained with ethidium bromide (in case of siRNA$^D$ only) and documented using a UVP bioimaging system. An LM-20E ultraviolet benchtop transilluminator (UVP, Upland, Calif.) was used in conjunction with an Olympus (Melville, N.Y.) Digital Camedia C-4000 zoom color camera with a UV filter and a lens. Documentation was completed using the DOC-IT system software.

Cell Culture: Human dopaminergic neuronal precursor (DAN) cells were obtained from Clonexpress, Inc (Gaithersburg, Md.). Actively growing population of cells were tested for tyrosine hydroxylase (TH) expression by immunocytochemistry. DAN cells are supplied with a proprietary growth factor supplement (DNCS) as a 100× stock solution, which is added to DMEM:F12(50:50) containing 5% FBS and 10 ng/ml of bFGF, and 5 ng/ml of GDNF to make DAN cell growth medium. These cells differentiate into neurons within a week, when plated on polylysine (PLL) coated plates at a density of approximately $10^4$ cells per sq.cm. in DMEM/F12 (50:50) supplemented with DNC5, 5% FBS, 10 ng/ml of bFGF, 10 ng/ml of EGF, and 100 uM dibuturyl cAMP.

Imaging of nanoparticles in vitro: The cellular uptake of the nanoparticle conjugated with DARPP-32 siRNA (siRNA$^D$) was visualized using Dark-Field microscopy. The light-scattering images were recorded using an upright Nikon Eclipse 800 microscope with a high numerical dark-field condenser (N.A. 1.20-1.43, oil immersion) and a 100/1.4 NA oil Iris objective (Cfi Plan Fluor). In the dark-field configuration, the condenser delivers a narrow beam of white light from a tungsten lamp and the high NA oil immersion objective collects only the scattered light from the samples. The dark-field imaging was captured using a QImaging Micropublisher 3.3 RTV color camera. The Qcapture software from the camera manufacturer was used for image acquisition and has a feature for adjusting the white color balance for accurately capturing the color differences in samples.

Fluorescence studies from cell lysates: DAN cells incubated with 100 pmols of free siRNA$^F$, as well as GNR-siRNA$^F$, and siPORT-siRNA$^F$ nanoplexes and 24 h later cells were processed for fluorescence measurements. The medium was removed and the cells were lysed using M-PER (Mammalian Protein Extraction Reagent-Pierce) and analyzed using a spectrofluorometer. siRNA$^F$ is non-specific siRNA used as a control. siRNA$^F$ was purchased from AMBION under catalog number 4650.

Cell viability assay: Cell viability assay measures the reduction of a tetrazolium component (3-(4,5-Dimethylthiazol-2-yl)-2,5-diphenyltetrazolium bromide, or MTT) into an insoluble formazan product by the mitochondria of viable cells. Cells in a 24 well plate (10,000 cells/ml/well) were incubated with the MTT reagent for approximately 3 hours, followed by addition of a detergent solution to lyse the cells and solubilize the colored crystals. The samples were read using an ELISA plate reader at 570 nm wavelength.

Transfection: Transgene expression is monitored at 24-96 hr post transfection and followed up to a period of 2 weeks post transfection. SiRNA delivery takes a minimum of 12-24 hr. An appropriate transfection reagent control and a scrambled sequence negative controls are used in all experiments. Twenty-four hours before siRNA transfection, $2\times10^5$ dopaminergic neuronal cells are seeded onto six-well plates in OPTI-MEM containing 4% FBS with no antibiotics to give 30 to 50% confluence at the time of transfections. The siRNA is reconstituted in DNase-RNase free water to a final concentration of 0.1 uM and mixed with 20 µl of solution of GNR synthesized as described above in a ratio empirically determined for each siRNA, incubated at room temperature for 15 min and used for in vitro transfection of dopaminergic neurons at a final concentration of 200 pmol of siRNA. Levels of mRNA were monitored at 12-120 hr post transfection and at up to 2 weeks. The commercially available siRNA delivery agent, siPORT (Ambion Inc, Austin Tex.) was used as the positive control in our experiments.

RNA extraction: Cytoplasmic RNA is extracted by an acid guanidinium-thiocyanate-phenol-chloroform method using Trizol reagent (INVITROGEN-LIFE TECHNOLOGIES, Carlsbad, Calif.) (Chomczynski P S N (1987) Anal Biochem. 162(1):156-159). The amount of RNA is quantitated using a Nano-Drop ND-1000 spectrophotometer (NANO-DROP™, Wilmington, Del.) and isolated RNA is stored at −80° C. until used.

Real time quantitative PCR (Q-PCR): Relative abundance of each mRNA species is quantitated using real time quantitative PCR using specific primers using the Brilliant® SYBR® green Q-PCR master mix from STRATAGENE (La Jolla, Calif.). RNA is reverse transcribed to cDNA using the reverse transcriptase kit from Promega (Madison, Wis.). Relative expression of mRNA species is calculated using the comparative threshold cycle number ($C_T$) method (Radonié et al. (2004) Biochem Biophys Res Commun 313(4):856-862; Bustin S A (2002) J Mol Endocrinol 1(29):23-3)}. All data are controlled for quantity of RNA input by performing measurements on an endogenous reference gene, β-actin.

Western Blot analysis: Total protein is extracted using Mammalian Protein Extraction Reagent (Pierce, Rockford, Ill.) and 20 μg of protein is loaded per lane and separated by a 4-20% SDS-Tris/glycine PAGE After blocking of nonspecific binding sites with 5% non fat milk, membranes are probed with commercially available monoclonal antibodies. Protein levels of DARPP-32, and ERK1 are measured in cell lysates from primary neuronal cells treated with GNR conjugated DARPP-32 siRNA using DARPP-32 antibody (Cell Signalling Technologies Inc, Danvers, Mass.) and antibodies against ERK1 (Santacruz, Biotech) respectively.

Immunocytochemistry staining: 10,000 DAN cells, treated with the various agents, were plated on 35 mm glass bottom Petri dishes with a 14 mm microwell (Mat Tek Corporation, Ashland, Mass.) and allowed to attach. Cells were then rinsed briefly in phosphate buffered saline (PBS) and then fixed in 100% ice cold methanol for 15 min at room temperature. After fixation cells were washed twice in ice cold PBS. Cells are then permeabilized by incubating them with PBS containing 0.5% saponin. Nonspecific binding was blocked using 1% BSA in PBS with 0.1% Tween 20 (PBST) for 30 min. Cells are then incubated in primary antibodies (DARPP-32 Antibody, Cell Signalling Technology; ERK1, Santacruz Biotech) diluted in 1% BSA in PBST for 1 hr at room temperature, washed with PBST and incubated with a Alexa Fluor 647 labelled secondary antibody. Nuclei are stained using DAPI (0.1 μg/ml) for 1 min, and coverslip mounted with a drop of aqueous mounting media).

In-vitro BBB model: The in-vitro BBB model used primary cultures of human BMVEC and Normal Human astrocytes (NHA), both of which were obtained from Applied Cell Biology Research Institute (ACBRI) Kirkland, Wash. Characterization of BMVEC demonstrated that >95% cells were positive for cytoplasmic VWF/Factor VIII. BMVEC were cultured in CS—C complete serum-free medium (ABCRI) with attachment factors (ABCRI) and Passage Reagent Group™ (ABCRI). NHAs were cultured in CS—C complete serum-free medium (ABCRI), supplemented with 10 μg/ml human EGF, 10 mg/ml insulin, 25 μg/ml progesterone, 50 mg/ml transferrin, 50 mg/ml gentamicin, 50 amphotericin, and 10% FBS, and characterized by >99% of these cells being positive for glial fibrillary acidic protein (GFAP). The BBB model, based on 2-compartments separated by a 3 micron Polyethylene Terephthalate (PET) insert (surface area=4.67 $cm^2$), was generated as described previously (Mahajan et al. (2008) Brain Research, 1203:133-148). Formation of an intact BBB was measured by determining transendothelial electrical resistance (TEER), using an ohm meter Millicell ERS system (MILLIPORE, Bedford, Mass.).

Transmigration assay: All transmigration experiments are conducted on day 6 of BBB culture Mahajan et al. (2008) Brain Research; 1203:133-148; Mahajan (2008) Tight Junction Regulation by Morphine and HIV-1 Tat Modulates Blood-Brain Barrier Permeability J of Clinical Immunology; Persidsky Y GH (1997) J Leukoc Biol 62(1):100-106. Fluorescence (FAM) labelled siRNA-GAPDH (or $siRNA^F$, Ambion), GNR-$siRNA^F$ nanoplexes, siPORT conjugated $siRNA^F$ and free GNR were added to the upper chamber of the in-vitro BBB, along with a fixed volume of media (2 ml) which was added to the upper and lower chambers. After addition of the $siRNA^F$, GNR-$siRNA^F$, siPORT-$siRNA^F$ and free GNR and incubation at 37° C. for 3 hrs, 1 ml of media was aspirated from both the upper and the lower chambers and analyzed spectrofluorometrically.

Example 2

Figure 8:
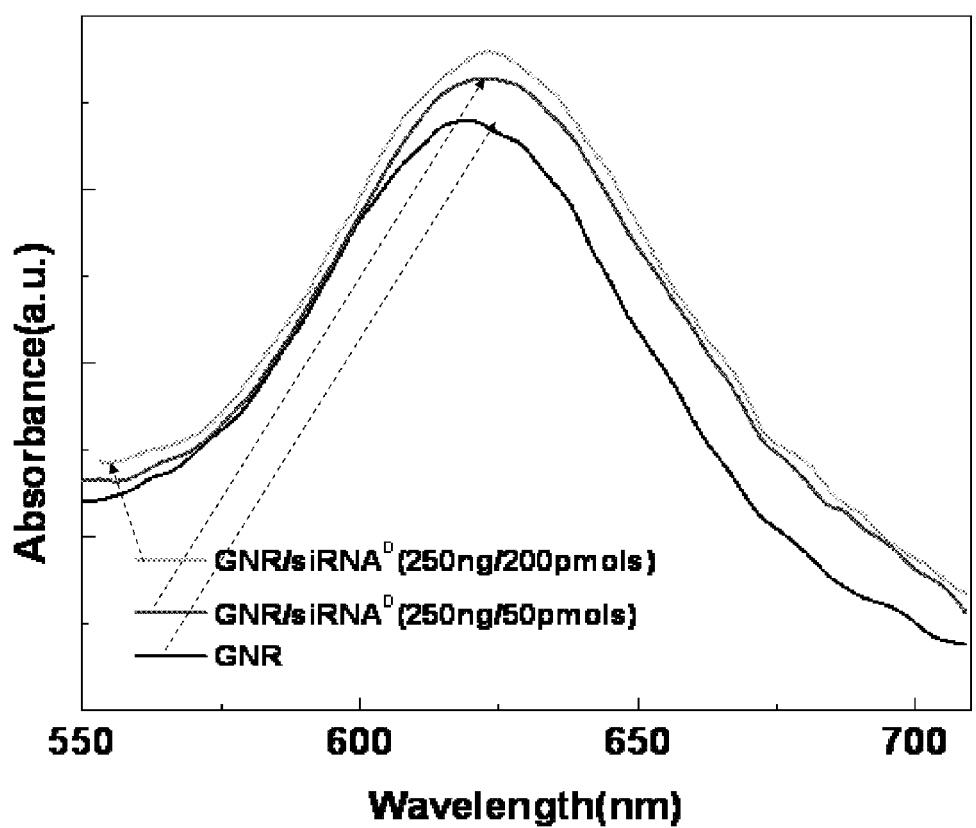
FIG. 8 provides a graphical representation of data showing the localized longitudinal surface Plasmon resonance peak of GNRs red-shift upon complexation with siRNA.

Electrostatic binding of siRNA with Gold nanorods to form nanoplexes: the cationic GNRs, prepared by growing multilayers of cationic polyelectrolytes upon cetyltrimethylammonium bromide (CTAB) coated GNRs, were electrostatically complexed to; (a) fluorescently labeled marker siRNA (siRNA-FAM; $siRNA^F$) for studying their binding with nanoparticles and subsequent cellular uptake, and (b) functional siRNA specific for DARPP-32 ($siRNA^D$). To examine the binding efficiency of the siRNA with the GNRs, we performed agarose gel electrophoresis. The results obtained for siRNA, both free and complexed with GNRs, are shown in FIGS. 8a and 8b. It is evident that siRNA complexed with nanoparticles (lanes 2, 3, and 4) does not have the same electrophoretic mobility as free siRNA (lane 1), and this restricted mobility is proportional to the amount of GNR complexed with siRNA. Also, we observed a partial quenching in the emission signal from both $siRNA^F$ (FIG. 8a) and ethidium bromide stained $siRNA^D$ (FIG. 8b) as a result of the complexation with the GNRs. These data indicate the successful complexation of siRNA with GNRs, and the highest loading of siRNA per GNRs can be calculated to be ~70 pmoles of siRNA per 1 μg of GNR. We also determined the effect of siRNA complexation on the overall size and morphology of the GNRs, using transmission electron microscopy (TEM) indicating that siRNA complexation did not cause any aggregation effect on the GNRs, and we have observed this stability for more than a month post complexation. Surface charge (zeta potential) measurements of the GNRs, without (average zeta potential of +21.6 mV) and with (average zeta potential of −4.4 mV) complexed siRNA, indicated that the anionic siRNA molecules saturate the surface of the otherwise cationic GNRs, leading to a sparsely negative net charge of the complex. The sparsely negative charge on their surface becomes significant when considering the well known fact that nanoparticles with neutral or slightly negative surface charge are known to evade capture by the reticuloendothelial system (RES) of the body, as well as avoid nonspecific interaction with physiological proteins and other biomolecules (Davis SS (1997) Trends Biotechnol 15(6):217-224).

Figure 9:
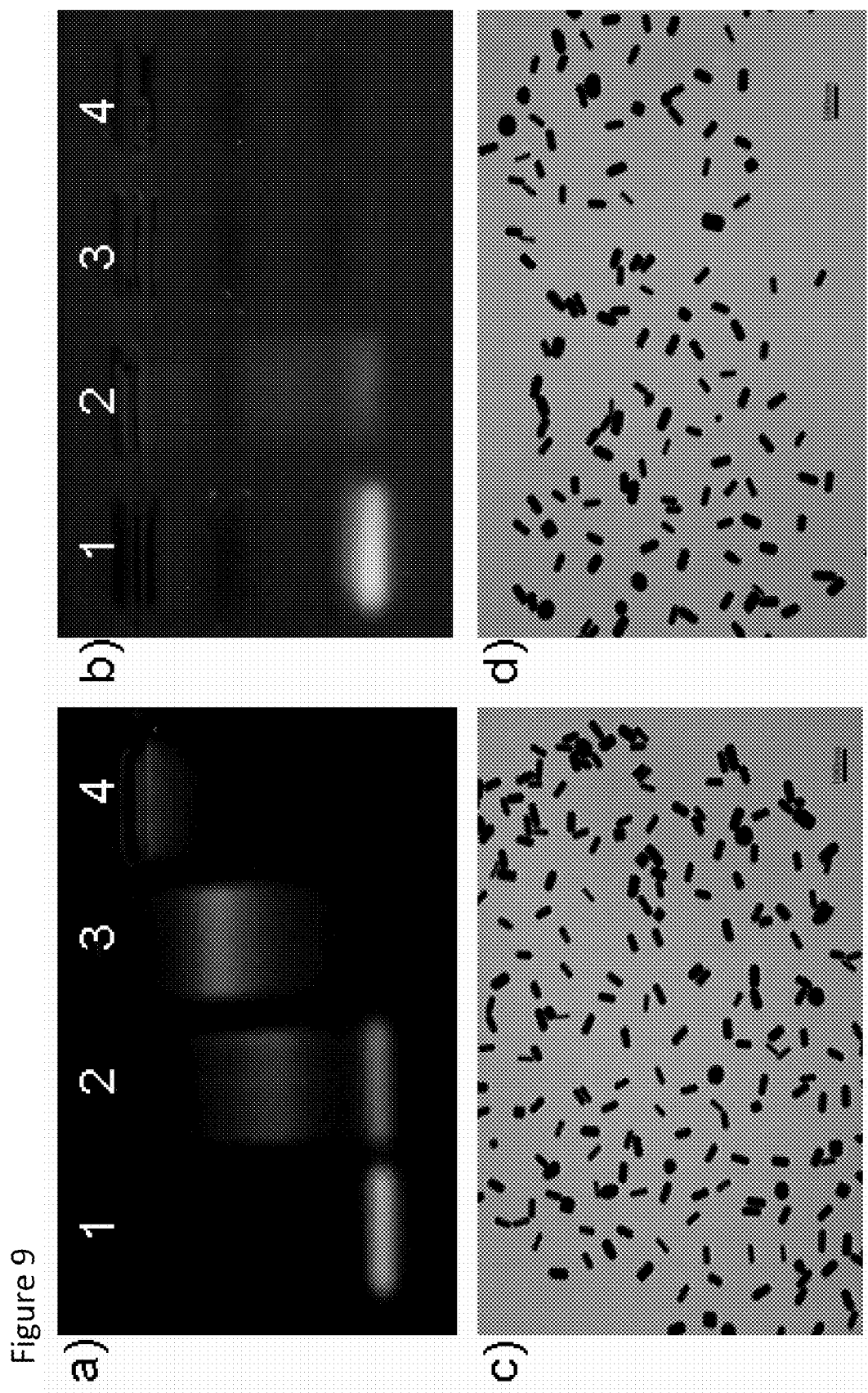
FIG. 9 provides photographic representations of data showing binding efficiency of siRNA$^F$ (a) and siRNA$^D$ (b) with GNR studied by agarose gel electrophoresis. Results show retarded mobility of the siRNA upon complexation with increasing amounts of GNRs. lane1: siRNA (50 pmols), lane2: GNR-siRNA (250 ng GNR/50 pmols siRNA), lane3: GNR-siRNA (500 ng GNR/50 pmols siRNA); lane4: GNR-siRNA (750 ng GNR/50 pmols siRNA); TEM images of (c) free GNR and (d) GNR-siRNA nanoplexes, showing no sign of aggregation of GNRs upon complexation with siRNA.

The complexation of siRNA with GNRs was confirmed by measuring the plasmonic shift of the GNRs. As shown in FIG. 9, the complexation with siRNA results in a ~5 nm red shift in the localized longitudinal surface plasmon resonance peak of the GNRs. This shift in the absorption spectra of GNRs is the result of changes in the local refractive indices around the GNRs, following complexation with siRNA molecules. Such plasmonic shift experiments can serve as a powerful nanotechnology based characterization tool for studying the interaction of gold nanoparticles/nanorods with biological molecules such as proteins and nucleic acids.

Example 3

Uptake of nanoplexes in neuronal cells in vitro, without any sign of cytotoxicity: The strong orange-red plasmonic scattering associated with GNRs can be utilized in studying cellular delivery using dark field microscopy. FIG. 1 shows the dark-field images of DAN cells, without (1c) and with (1a) treatment with the GNR-siRNA$^D$ nanoplex. The cellular uptake of the nanoplexes can be easily observed from the strong orange-red scattering of the nanoplex treated, as opposed to the untreated, DAN cells. This experiment highlights another advantage of using nanotechnology in the delivery of therapeutics, where in addition to the therapeutic efficacy, the unique properties of the GNRs can be used to determine their uptake in cells using dark-field imaging.

Figure 10:
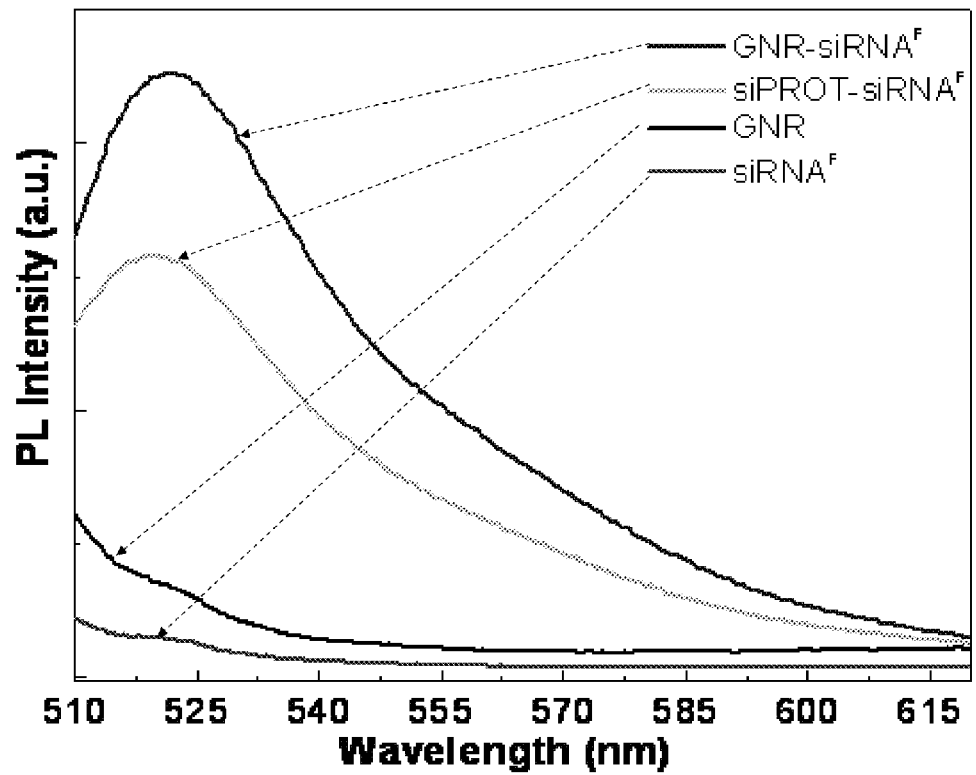
FIG. 10 provides a graphical representation of data showing fluorescence spectra of siRNA$^F$ taken from lysates of DAN cells after transfection using GNR-siRNA$^F$ nanoplexes, SiPORT-siRNA$^F$ complex, free siRNA$^F$ and GNRs only. Data shows transfection with the GNR-siRNA$^F$ nanoplexes result in the highest cellular uptake.

Confocal microscopy was also used in order to confirm the cellular entry of the nanoplexes in DAN cells, using GNR-siRNAF nanoplex. The confocal images of DAN cells treated with either siRNA$^F$ alone (FIG. 1d), or with GNR-siRNA$^F$ nanoplex (FIG. 1b), demonstrate strong fluorescence signal from the treated, as opposed to untreated, DAN cells. We also measured fluorescence from cellular lysates following their treatment with siRNA$^F$, either free, or complexed with GNRs or complexed with the commercially available gene silencing agent sold under the trade name siPORT™ by AMBION (FIG. 10). Our results indicate that while lysates from cells treated with free siRNA$^F$ show little or no fluorescence, the fluorescence from lysates of cells treated with GNR-siRNA$^F$ is approximately three times higher than that obtained from cells treated with siPORT-siRNA$^F$ indicating that the intracellular delivery efficiency of siRNA using GNRs is superior to that using this commercially available gene silencing agent.

Figure 11:
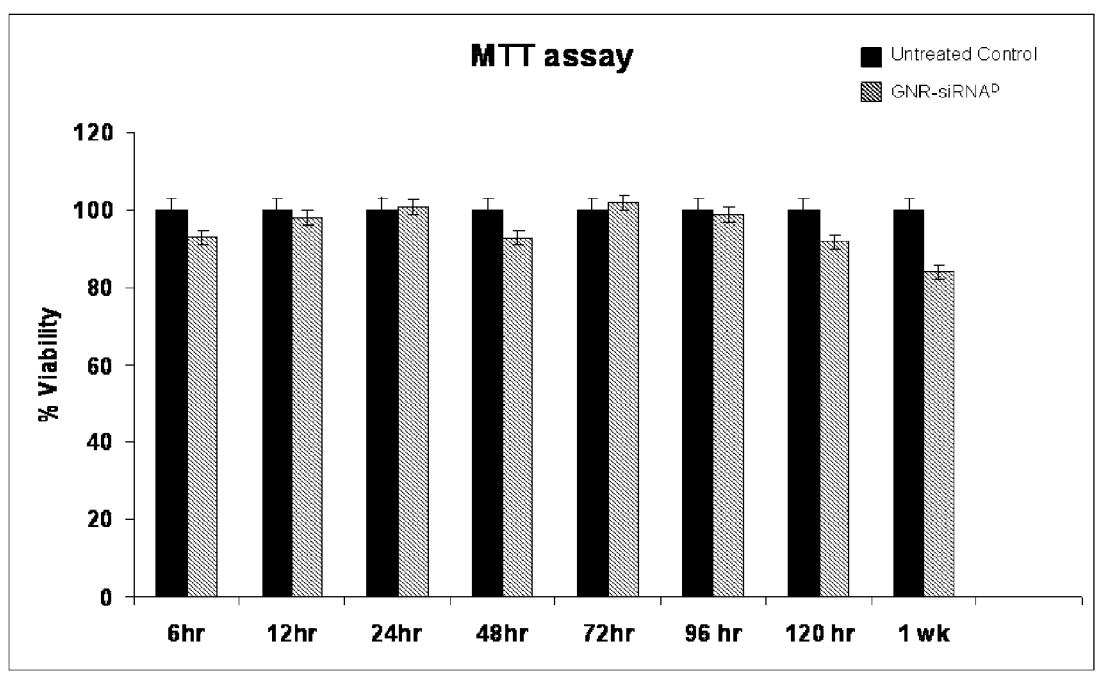
FIG. 11 provides a graphical representation of data showing cell viability (MTT) assay of DAN cells following treatment with GNR-siRNA$^D$ nanoplexes for various time points. Results show no indication of toxic effects on the cells following treatment with the nanoplexes, which were observed up to one week post treatment. The results are the mean±SD of 3 separate experiments.

We also investigated the potential cytotoxic effects of these nano-complexes, and found that the DAN cells treated with GNR-siRNA maintained 98% viability, even after 1 week post treatment (FIG. 11). From these data, it can be concluded that these nanocomplexes are not toxic to cells.

Example 4

Knockdown of DARPP-32 gene following treatment with GNR-siRNA$^D$ nanoplexes. Opiate addiction involves activation of the dopaminergic signalling pathway in the brain, in which adenosine 3',5'-monophosphate-regulated phosphoprotein (DARPP-32) plays a significant role (Greengard P. et al. (1999) Neuron. 23:435-447; Greengard et al. (1998) Brain Res Rev. 26(2-3):274-284; Gould TD MH (2005) Proc Natl Acad Sci 102(2):253-254). Neurotransmitters such as dopamine activate protein kinase A (PKA)-mediated phosphorylation of DARPP-32. Recently, it has been implicated that both dopamine and glutamate receptors induced modulation of DARPP-32, resulting in the activation of the extracellular signal-regulated kinase (ERK) mitogen-activated protein (MAP) kinase cascades (Valjent et al. (2001) (Humana Press Inc), Vol 23, pp 83-99; Valjent et al. (2005) Med Sci (Paris) 21(5):453-454; Valjent et al. (2005) Proc. Natl. Acad. Sci. U.S.A. 102(2):491-496. ERK activity has been known to be important in neuronal plasticity and its pharmacologic blockade prevents the transcriptional and behavioural effects of various drugs of abuse. All the above observations indicate that the DARPP-32 is the central molecular "trigger" which underlies the neurobiological alterations related to drug abuse. Therefore, it is expected that the suppression of DARPP-32 gene expression using delivery of its siRNA antagonist in dopaminergic neuronal (DAN) cells will lead to significant behavioral inhibition of the drug addiction process.

Figure 2:
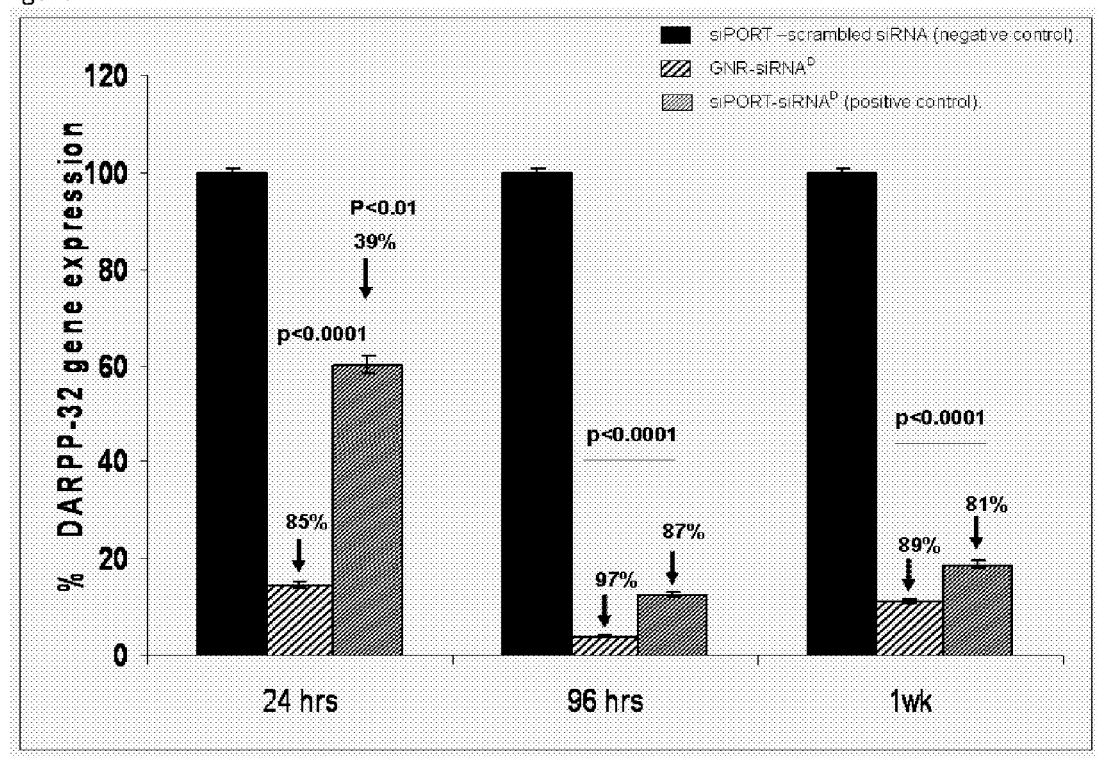
FIG. 2 provides graphical representations of data showing the efficiency of DARPP-32 gene expression inhibition in DAN cells using siRNA against DARPP-32 (siRNA$^D$), following complexation with GNRs (nanoplex), or the commercial agent siPORT. Quantitative real-time PCR (QPCR) data showing a >80% suppression in DARPP-32 gene expression in DAN cells that were transfected with the nanoplex. Relative expression of mRNA species was calculated using the comparative CT method. Data are the mean±SD of 3 separate experiments done in duplicate. Statistical significance was determined using ANOVA based on comparison between, the siPORT-siRNA$^D$ (positive control), GNR-siRNA$^D$ nanoplex and the siPORT with scrambled siRNA (negative control). A significant decrease in DARPP-32 gene expression was observed up to 1 week post transfection, with maximum suppression observed at 96 hrs post transfection.
Figure 3:
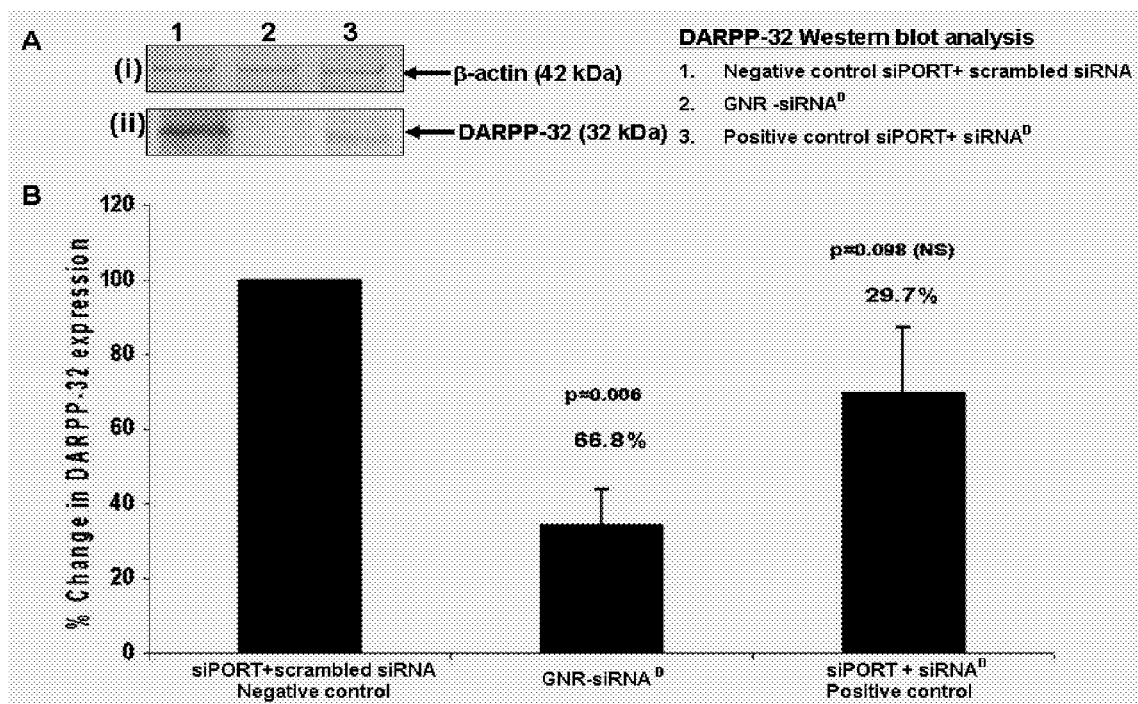
FIG. 3 provides graphical and photographic representations of data showing the effect of the GNR-siRNA$^D$ nanoplex on DARPP-32 protein expression in DAN cells. Western blot analysis of DARPP-32 protein from lysates of DAN cells following their treatment in vitro with GNR-siRNA$^D$ nanoplexes (Lane 2), as well as both siPORT positive control (Lane 3) and negative control (Lane 1), at 120 hrs post-transfection. Panel A shows data from a representative western blot experiment showing (i) no change in b-actin (42 kDa band) protein expression, and (ii) a significant decrease in DARPP-32 (32 kDa band) protein expression, in cells treated with the GNR-siRNA$^D$ nanoplex (Lane 2), as opposed to cells treated with negative control (siPORT-scrambled siRNA, Lane 1). Panel B: Graphical representation of the densitometric analysis of the DARPP-32 protein band showing percentage decrease in the DARPP-32 protein expression in cells treated with GNR-siRNA$^D$ and siPORT-siRNA$^D$, when compared with that in cells treated with siPORT-scrambled siRNA (negative control, arbitratily assigned with 100% DARPP-32 expression). Data shown are mean±SD of results from 3 separate experiments, and statistical significance was determined using ANOVA. Results show a significant decrease in DARPP-32 protein expression in the GNR-siRNA$^D$ (66.8% decrease) treated cells, significantly higher than that obtained from siPORT-siRNA$^D$ (29.7% decrease) treated cells.

To test inhibition of expression of the DARPP-32 target gene, DAN cells were incubated with the GNR-siRNA$^D$ nanoplexes and the efficiency of gene silencing was determined by measuring the percent inhibition of the expression of DARPP-32 using quantitative real time (Q)-PCR and Western Blot. Results from these experiments show that significant inhibition (>80%) of DARPP-32 expression was produced in the DAN cells (FIG. 2) and this knockdown was observed up to one week post-transfection. In comparison to the commercial agent siPORT, it was found that the GNR-siRNA$^D$ nanoplexes have superior gene silencing efficacy all the time points post-transfection, particularly at the onset (24 hours post-transfection) of the gene silencing process. The efficient silencing of DARPP-32 gene using GNR mediated siRNA delivery was further confirmed by investigating the down-regulation of the DARPP-32 protein using Western Blot analysis (FIG. 3). Our results show ~67% knockdown of protein expression DARPP-32 with GNR-siRNA$^D$ nanoplexes after 120 hrs post-transfection, higher than that obtained using the siPORT-siRNA$^D$ complex (~30% knockdown). Thus the superior gene silencing efficacy of these nanoplexes over that of the commercial agent siPORT-siRNA complexes have been validated using two independent methods. This enhanced gene silencing efficiency of nanoplexes over siPORT-siRNA complex directly correlates with the enhanced cellular delivery of siRNA using the GNRs over that using siPORT (FIG. 10).

Example 5

Figure 4:
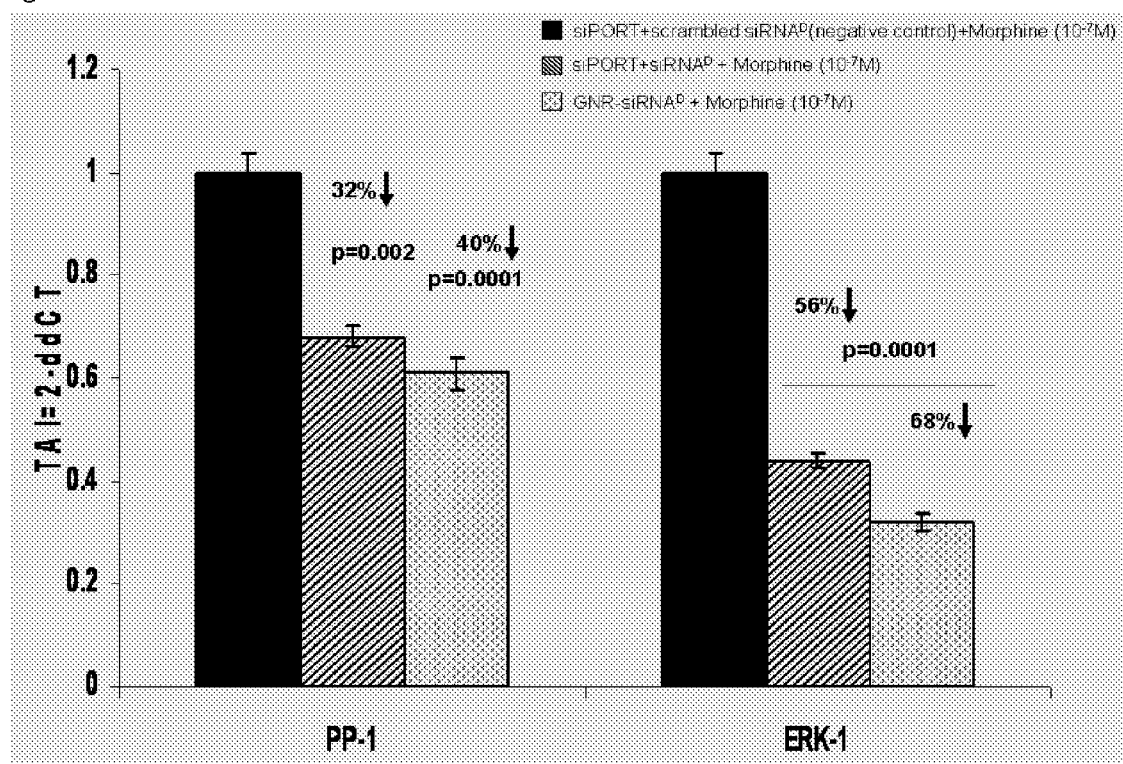
FIG. 4 provides graphical representations of data showing modulation of gene expression of effector molecules downstream of DARPP-32 (PP-1 and ERK-1) in siRNA$^D$ transfected DAN cells. Q-PCR data shows a significant decrease in both PP-1 and ERK-1 gene expression in DAN cells following treatment with GNR-siRNA$^D$ nanoplexes. Data are the mean±SD of 3 separate experiments done in duplicate. Statistical significance was determined using ANOVA based on comparison between the GNR-siRNA$^D$ and siPORT-siRNA$^D$ (positive control) samples with the siPORT-scrambled siRNA (negative control).

Knockdown of effector molecules (PP-1 and ERK) downstream of DARPP-32 following treatment with GNR-siRNA$^D$ nanoplexes: To evaluate whether the GNR-mediated DARPP-32 gene silencing will have further biological effects, we investigated the effect of DARPP-32 silencing on effector molecules such as PP-1 and ERK, which are downstream to DARPP-32 in the opiate signalling pathway. Here, using Q-PCR analysis, we measured the levels of PP-1 and ERK mRNA from DAN cells, which were treated first with the various transfection reagents for 24 hrs, then with morphine ($10^{-7}$M) overnight. The results (FIG. 4) demonstrate a substantial knockdown of both PP1 (~40%) and ERK (~68%) genes using the GNR-siRNA$^D$ nanoplexes, which are superior to that obtained using siPORT-siRNA$^D$. These data indicate that silencing of DARPP-32 by GNR conjugated siRNA$^D$ resulted in a significant decrease in the gene expression of downstream effector molecules, therefore showing that the DARPP-32 gene has functional relevance as an important signalling intermediate in the molecular mechanism underlying the development of drug addiction.

Figure 5:
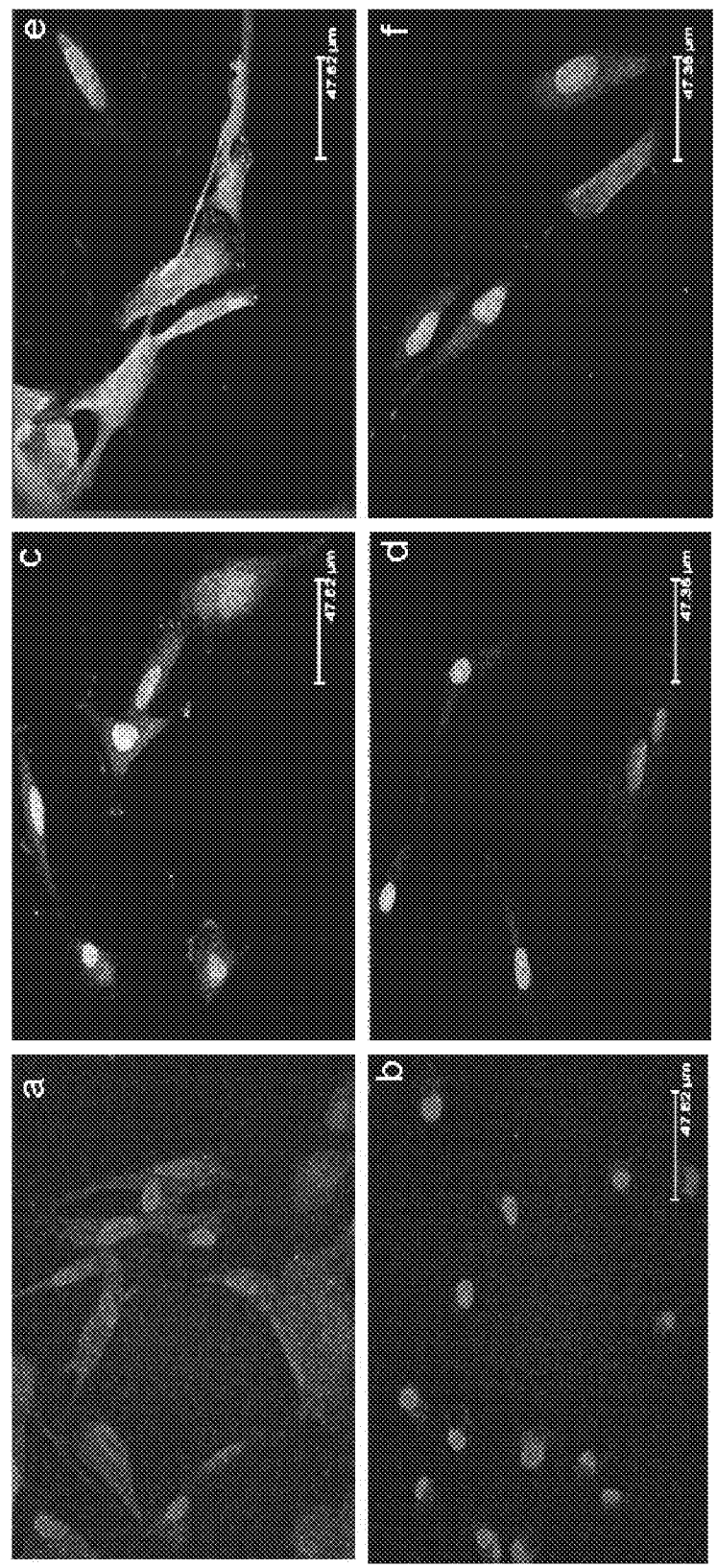
FIG. 5 provides imaging analysis of immunofluorescent studies on neuronal cells. Immunofluorescent staining for DARPP-32 (a-d) and ERK-1 (e & f) in transfected and non-transfected DAN cells. a: DARPP-32 expression in non-transfected DAN cells; b: DARPP-32 expression in GNR-siRNA$^D$ nanoplex transfected DAN cells. c: Morphine ($10^{-7}$ M) treated but non-transfected DAN cells; d: Morphine ($10^{-7}$M) treated DAN cells, transfected with GNR-siRNA$^D$; e: Morphine ($10^{-7}$M) treated untransfected DAN cells showing ERK-1 expression; f: Morphine ($10^{-7}$M) treated GNR-siRNA$^D$ transfected DAN cells showing ERK-1 expression. Our results show (a) morphine treatment enhances the DARPP-32 levels, and (b) GNR mediated transfection of siRNA against DARPP-32 reduces not only the levels of DARPP-32 expression, but also the expression of its downstream effector molecule ERK-1 in DAN cells.

Using immunofluorescent staining, we also investigated the effect of the stimulator morphine (drug of abuse), as well as the antagonist GNR-siRNA$^D$ nanoplex, on the expression of DARPP-32 and the downstream effector protein ERK-1 in DAN cells. We found that in the morphine treated DAN cells, the expression of DARPP-32 is enhanced when compared to the untreated control (FIG. 5, $a$ & $c$, respectively). Subsequent treatment of the morphine-treated DAN cells with GNR-siRNA$^D$ nanoplexes resulted in a reduction of the DARPP-32 levels to background signal (FIG. 5, $d$). A similar reduction of ERK was also observed in the morphine-treated DAN cells following treatment with GNR-siRNA$^D$ nanoplexes (FIG. 5, $e$ and $f$, respectively). These results indicate that morphine treatment enhances the DARPP-32 levels in the DAN cells and GNR mediated transfection of siRNA$^D$ reduces not only the levels of DARPP-32 expression, but also the expression of its downstream effector molecule ERK-1. These results further highlight the potential of GNRs to serve as a siRNA delivery vehicle for functional gene silencing.

Example 6

Figure 6:
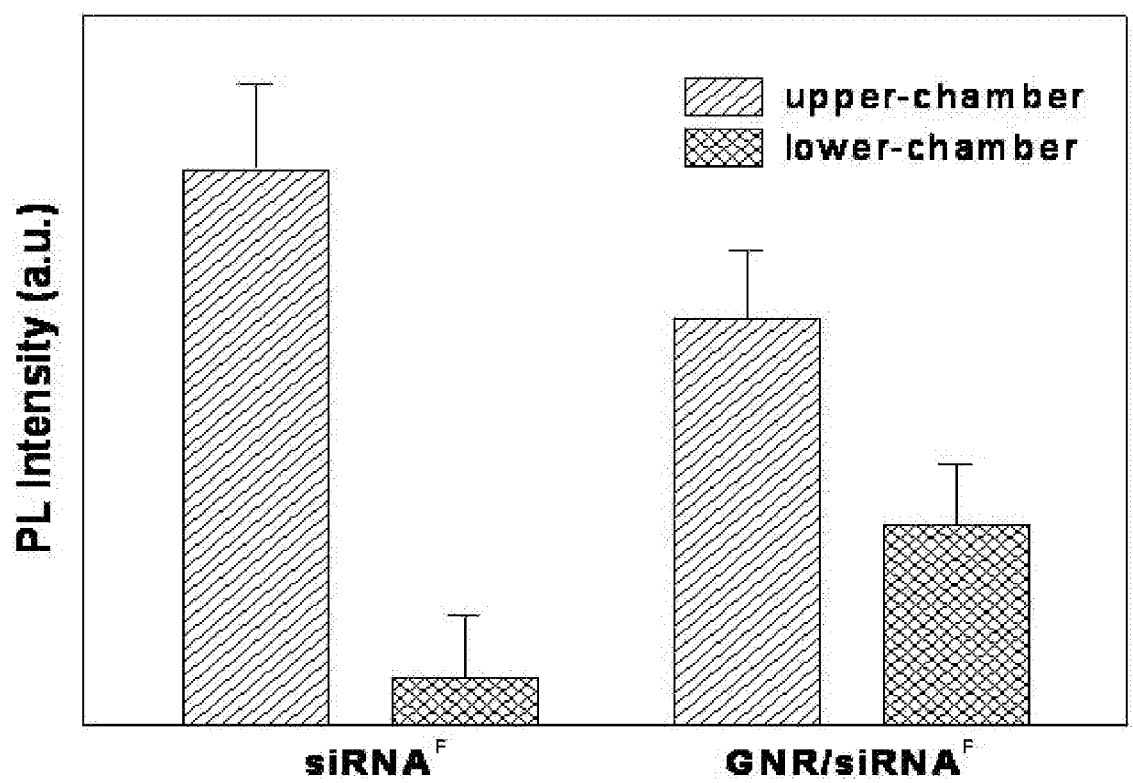
FIG. 6 provides graphical representations of data showing transmigration of GNR-siRNA$^F$ nanoplex across a brain blood barrier model. Fluorescence signal distribution collected from BBB model in upper-chamber (blood-end) and lower chamber (brain-end) of an in vitro BBB model, following treatment with free siRNA$^F$ and GNR-siRNA$^F$ nanoplex. Results show enhanced transmigration efficiency of the GNR-siRNA$^F$ nanoplex when compared to that of free siRNA$^F$.

Transmigration of GNR-siRNA$^F$ nanoplexes across an in vitro model of BBB: Since brain is the target organ for the application of DARPP-32 gene silencing and the BBB is a major impediment towards the brain specific non-invasive delivery of therapeutic agents, we used an established in vitro BBB model to determine the ability of GNR-siRNA nanoplexes to cross the BBB. Our results show that four hours after incubation of GNR-siRNA$^F$ in the upper chamber (venous side) of the BBB model, nearly 40% of the original fluorescence can be recovered in the lower chamber (brain-side) of the model (FIG. 6$a$). Using similar conditions with free siRNA$^F$, only 1% of the original fluorescence was recovered in the lower chamber (FIG. 6$b$). This result shows that the transmigration efficiency of siRNA across BBB increases significantly following complexation with GNRs. Furthermore, no change was observed in the trans-endothelial electrical resistance (TEER) values of the BBB, before (214±2.52 ohm/cm$^2$) and after (211.33±2.80 ohm/cm$^2$) treatment with the GNR-siRNA nanoplexes. Since TEER values indicate the functional integrity of the BBB, the above data shows that the GNR-siRNA$^F$ nanoplexes did not cause any functional damage to the BBB while traversing through this barrier.

TABLE 1

|  | Pre-treatment | Post-treatment |
| --- | --- | --- |
| GNR-siRNA$^D$ | 214 ± 2.52 | 211.33 ± 2.80 |

Example 7

This Example demonstrates in vivo inhibition of a target gene using the present invention.

Figure 7:
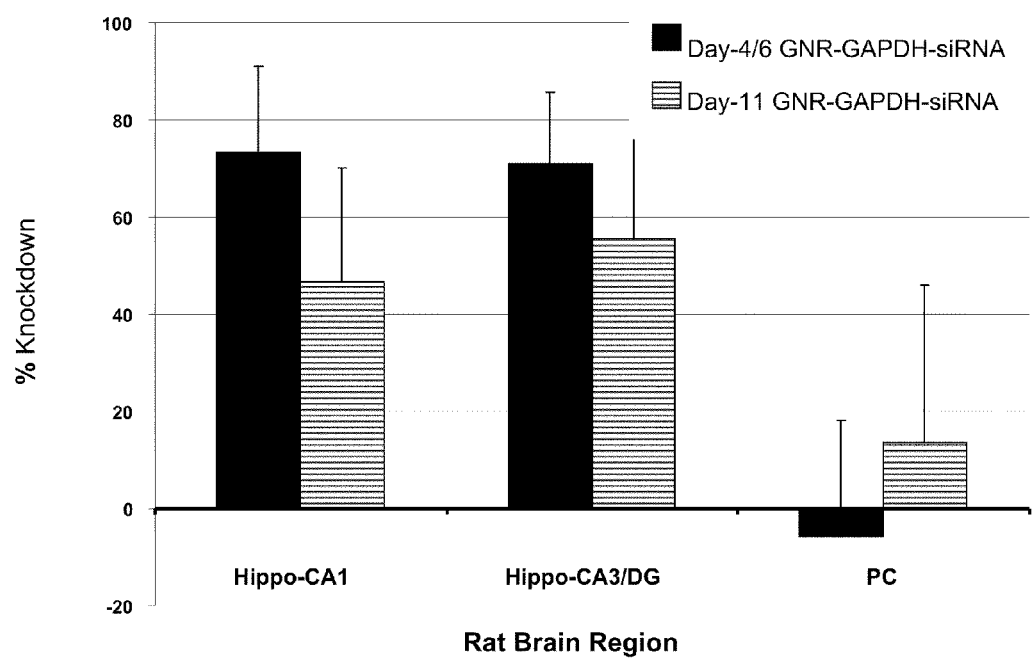
FIG. 7 provides a graphical representation of data showing Q-RT-PCR results demonstrating inhibition of GAPDH gene expression in vivo using GNR-GAPDH siRNACy3 in the rat hippocampus. Hippo, hippocampus; DG, dentate gyms; PC, parietal cortex.

FIG. 7 provides a graphical representation of Q-RT-PCR results. The data demonstrate inhibition of GAPDH gene expression using GNR-GAPDH siRNACy3 in the rat hippocampus.

To obtain the data presented in FIG. 7, a single microinjection (6 µl; 0.5 µl/min) of GNR-GAPDH electrostatically complexed to a commercially available siRNA targeted to GAPDH (siRNACy3 (purchased from APPLIED BIOSCIENCES, catalog number 4649, Silencer Cy3 labeled GAPDH siRNA (500 ng/l nmol)) was administered into the CA1 region of the right hippocampus. The Q-RT-PCR data shows >70% suppression of GAPDH gene expression in the CA1 region and in the combined CA3/dentate gyms regions of the hippocampus at 4 days post-injection. This level of suppression was maintained for up to 11 days post-injection. The brain region overlying the injection site, part of the parietal cortex, was used as a control region for diffusion. Results are expressed as the mean±SEM with the n number indicated in parentheses. Binding of siRNA with GNRs and loading efficiency was monitored by agarose gel electrophoresis mobility.

While the invention has been described through illustrative examples, routine modifications will be apparent to those skilled in the art, which modifications are intended to be within the scope of the invention.

---

We claim:

1. A method for inhibiting expression of a target gene in an individual, the method comprising administering to the individual an effective amount of a composition comprising surface functionalized gold nanorods electrostatically complexed to siRNA that can inhibit expression of the target gene via RNA interference (RNAi), wherein the siRNA is not covalently bound to the surface functionalized gold nanorods, wherein the composition comprises in a ratio 0.3-0.5 pmols of the surface functionalized gold nanorods for every 50 pmols of the siRNA, and wherein the administering the composition to the individual results in inhibited expression of the target gene.

2. The method of claim 1, wherein the siRNA comprises a sense strand and an antisense strand, wherein each of the sense strand and antisense strand consists of from 21-29 nucleotides.

3. The method of claim 2, wherein the surface functionalized gold nanorods are from 10 to 100 nm in length and are from 5 to 45 nm in diameter.

4. The method of claim 1, wherein the zeta potential of the surface functionalized gold nanorods electrostatically complexed to the siRNA is 3.9 to 0.7 mV at a pH of 7.0.

5. The method of claim 4, wherein the surface of the functionalized gold nanorods are functionalized by sequential coating with poly(3,4-ethylenedioxythiophene)/poly(styrenesulfate) (PEDT/PSS) and poly(diallyldimethyl ammonium chloride) (PDDAC).

6. The method of claim 1, wherein the siRNA dissociates from the surface functionalized gold nanorods gold nanorods in an intracellular aqueous medium in a cell of the individual, wherein the aqueous medium has a pH of from 4.0 to 6.0.

7. The method of claim 1, wherein the inhibiting the expression of the target gene comprises reducing an amount of mRNA encoded by the target gene in a plurality of cells in the individual by at least 60%, relative to the amount of mRNA encoded by the target gene in the plurality of cells prior to the administering the composition to the individual.

\* \* \* \* \*